United States Patent
Stephens (10) Patent No.: US 10,899,728 B2
(45) Date of Patent: Jan. 26, 2021

(54) SYSTEM, METHOD AND APPARATUS FOR CANNABINOID MIXTURE SEPARATION AND SOLVENT RECOVERY

(71) Applicant: Delta Separations LLC, Cotati, CA (US)

(72) Inventor: Benjamin K. Stephens, Santa Rosa, CA (US)

(73) Assignee: Delta Separations, LLC, Cotati, CA (US)

( * ) Notice: Subject to any disclaimer, the term of this patent is extended or adjusted under 35 U.S.C. 154(b) by 0 days.

(21) Appl. No.: 16/837,776

(22) Filed: Apr. 1, 2020

(65) Prior Publication Data

US 2020/0308134 A1    Oct. 1, 2020

Related U.S. Application Data

(60) Provisional application No. 62/827,426, filed on Apr. 1, 2019.

(51) Int. Cl.
*B01D 11/02*     (2006.01)
*C07D 311/80*    (2006.01)

(52) U.S. Cl.
CPC .................. *C07D 311/80* (2013.01)

(58) Field of Classification Search
None
See application file for complete search history.

(56) References Cited

U.S. PATENT DOCUMENTS

| | | | | |
|---|---|---|---|---|
| 5,901,574 | A * | 5/1999 | Rohde | F25J 5/005 62/640 |
| 9,987,567 | B1 * | 6/2018 | Ko | C07C 37/86 |
| 2018/0078874 | A1 * | 3/2018 | Thomas | B01D 53/1418 |
| 2018/0282250 | A1 * | 10/2018 | Rutz | B01D 11/02 |
| 2019/0143246 | A1 | 5/2019 | Ko | |

OTHER PUBLICATIONS

The International Searching Authority, Notification of Transmittal of the International Search Report and the Written Opinion of the International Searching Authority dated Jun. 29, 2020 for International Application No. PCT/US2020/26245, 10 pages.

* cited by examiner

*Primary Examiner* — Russell G Fiebig
(74) *Attorney, Agent, or Firm* — Dickinson Wright, PLLC; Michael E. Noe, Jr.

(57) ABSTRACT

A system for processing cannabinoids and recovering solvent has a vessel for a mixture of cannabinoids and solvent. A pump forms a vacuum in the system to draw the mixture into a first heat exchanger to pre-heat the mixture. A falling film evaporator receives the mixture from the first heat exchanger, and boils the mixture to form a solvent vapor. The falling film evaporator collects the cannabinoids from the mixture as a crude oil. The first heat exchanger receives the solvent vapor. Heat is transferred to incoming mixture of the system, and cools and condenses the solvent vapor to form solvent condensate and vapor. A second heat exchanger receives and further cools the solvent condensate and vapor to form further condensed solvent and some solvent vapor. The pump receives the further condensed solvent and some solvent vapor and increases pressure to form solvent liquid and recovers solvent liquid for reuse.

19 Claims, 6 Drawing Sheets

SYSTEM, METHOD AND APPARATUS FOR CANNABINOID MIXTURE SEPARATION AND SOLVENT RECOVERY

CROSS-REFERENCE TO RELATED APPLICATION

This application claims priority to and the benefit of U.S. Prov. Pat. App. No. 62/827,426, filed Apr. 1, 2019, which is incorporated herein by reference in its entirety.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

BACKGROUND

1. Field of the Disclosure

The present disclosure generally relates to processing plant material. More specifically, the present disclosure relates to a continuous system, method and apparatus for separating plant products from solvent, and recovering the solvent for reuse.

2. Description of the Related Art

Hashish is a consumable *Cannabis* concentrate composed of compressed, cannabinoid-rich resin glands, called trichomes. The trichomes are found on the flowers, and to a lesser extent, in the stems and leaves of the plant.

Historically, separating the cannabinoids from the plant has been very difficult as the cannabinoid resin is quite sticky. Processors of these plants use solvents to assist in the separation or extraction of the cannabinoids. Examples of the solvents include alcohol, such as ethanol. The resulting product is a cannabinoid mixture, such as a solution or tincture, having cannabinoids contained in the solvent liquid. Subsequent steps include separating the cannabinoids from the solvent, which can be challenging and are usually very inefficient and energy intensive. Conventional processes generally rely on a distillation method that generates so much heat that a large chiller is required to neutralize the heat. The chiller consumes significant energy to safely complete the processing. Although these solutions are workable, improvements in processing plant material continue to be of interest.

SUMMARY

Embodiments of a system, method and apparatus for processing plant material are disclosed. For example, a system for processing cannabinoids and recovering solvent can include a vessel configured to contain a mixture comprising cannabinoids and solvent. A pump can be configured to form a vacuum in the system to draw the mixture into a first heat exchanger configured to pre-heat the mixture to less than a boiling point of the solvent. A falling film evaporator can be configured to receive the mixture from the first heat exchanger, heat the mixture above the boiling point of the solvent, and boil the mixture to form a solvent vapor. The falling film evaporator can be configured to collect the cannabinoids from the mixture as a crude oil. The first heat exchanger can be configured to receive the solvent vapor. The system can be configured to transfer heat to incoming mixture of the system, thereby configured to cool and condense the solvent vapor to not greater than the boiling point of the solvent to form solvent condensate and vapor. A second heat exchanger can be configured to receive and further cool the solvent condensate and vapor to form further condensed solvent and some solvent vapor. In addition, the pump can be configured to receive the further condensed solvent and some solvent vapor and increase pressure to increase the boiling point of the solvent to form solvent liquid, such that the system is configured to recover solvent liquid for reuse.

In another example, a method for processing cannabinoids and recovering solvent can be provided. The method can include forming a mixture comprising cannabinoids and solvent; using a pump to form a vacuum in a system, drawing the mixture into a first heat exchanger and preheating the mixture to less than a boiling point of the solvent; drawing the mixture into a falling film evaporator, heating the mixture above the boiling point of the solvent, and boiling the mixture to form a solvent vapor; collecting the cannabinoids from the mixture as a crude oil at a bottom of the falling film evaporator; drawing the solvent vapor to the first heat exchanger; transferring heat to incoming mixture of the system, thereby cooling and condensing the solvent vapor to not greater than the boiling point of the solvent to form solvent condensate and vapor; drawing and further cooling the solvent condensate and vapor in a second heat exchanger to form further condensed solvent and some solvent vapor; drawing the further condensed solvent and some solvent vapor to the pump and increasing pressure to increase the boiling point of the solvent to form solvent liquid; and then drawing the solvent liquid to a third heat exchanger, cooling the solvent liquid and recovering the cooled solvent liquid for reuse.

BRIEF DESCRIPTION OF THE DRAWINGS

A more complete understanding of the present disclosure may be derived by referring to the detailed description and claims when considered in connection with the figures, wherein like reference numbers refer to similar items throughout the figures.

DETAILED DESCRIPTION

In the following detailed description, reference is made to the accompanying drawings that form a part of the disclosure. The drawings show by way of illustration, and not of limitation, embodiments by which the disclosure may be practiced. The drawings, the foregoing discussion, and the following description are exemplary and explanatory only.

They are not intended to limit the scope of the disclosure or its application in any manner.

FIGS. 1-6 illustrate embodiments of a system, method and apparatus for processing plant material. For example, the system can include a falling film evaporator 101, and one or more heat exchangers (e.g., three shown) 102, 103, and 104. In some versions, the equipment can include a hot water heater 405 (FIG. 4), a water cooler 406, a chiller 407 and a pump 105. Examples of these components can be connected by conduits, such as stainless steel tubing 106 (FIG. 1), such as commercially available 316L SS sanitary tubing and fittings. One example of FFE 101 can be a GEA Falling Film Evaporator from Columbia, Md. Examples of the heat exchanges 102, 103, 104 can include Plate Heat Exchangers, Model #AlfaNova 76-30H of Alfa Laval Inc. in Richmond, Va. One example of hot water heater 405 can be a Mokon Duratherm Model-DT Series, of Buffalo, N.Y. An example of water cooler 406 can be a MTA TAEevoTech 051, of Amherst, N.Y. One example of chiller 407 can be a Poly-Science Durachill 6800, of Niles, Ill. An example of the pump 105 can be a Flowserve Liquid Ring Pump series SiHI LPHX/LPH, of Irvine, Tex.

Figure 1:
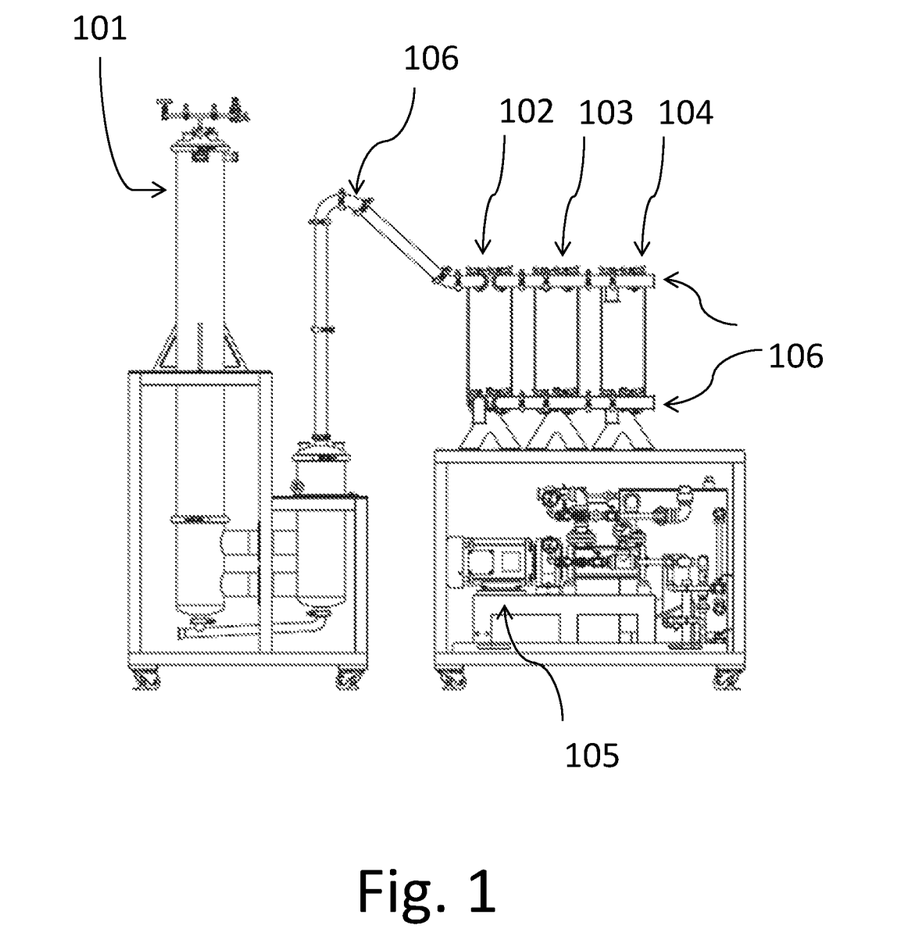
FIG. 1 is a front view of an embodiment of components of a system for processing plant material.
Figure 2:
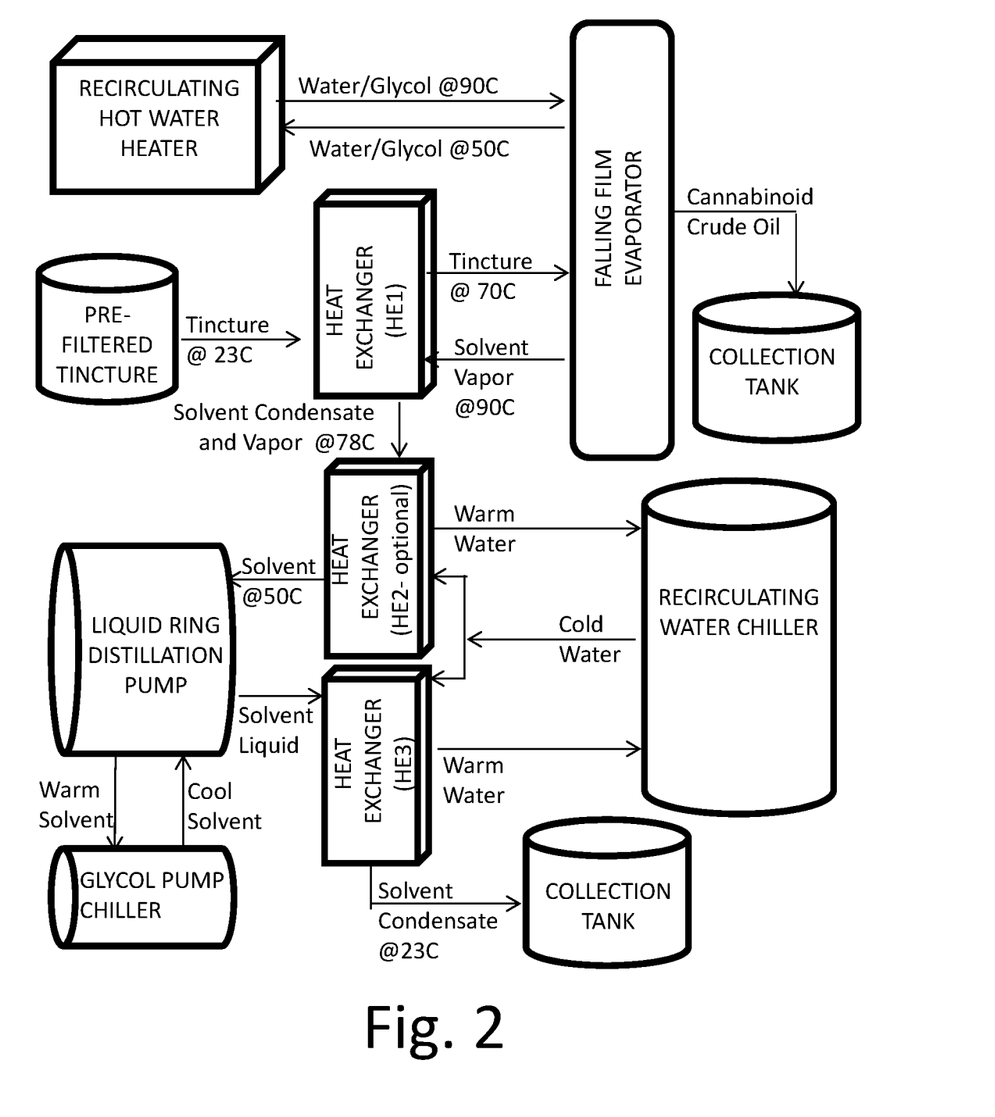
FIG. 2 is a schematic view of an embodiment of components of the system and the flow of fluids between them.
Figure 3:
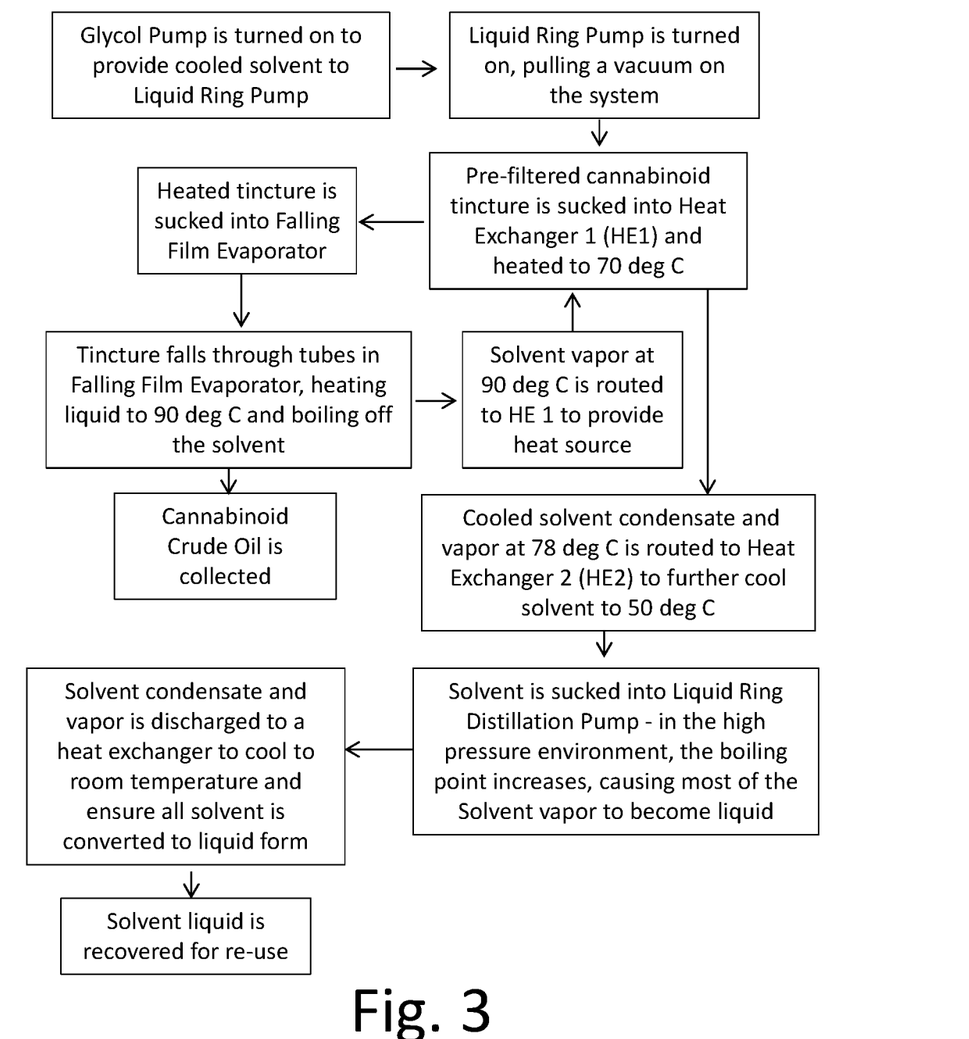
FIG. 3 is a flow chart of one embodiment of the process.
Figure 4:
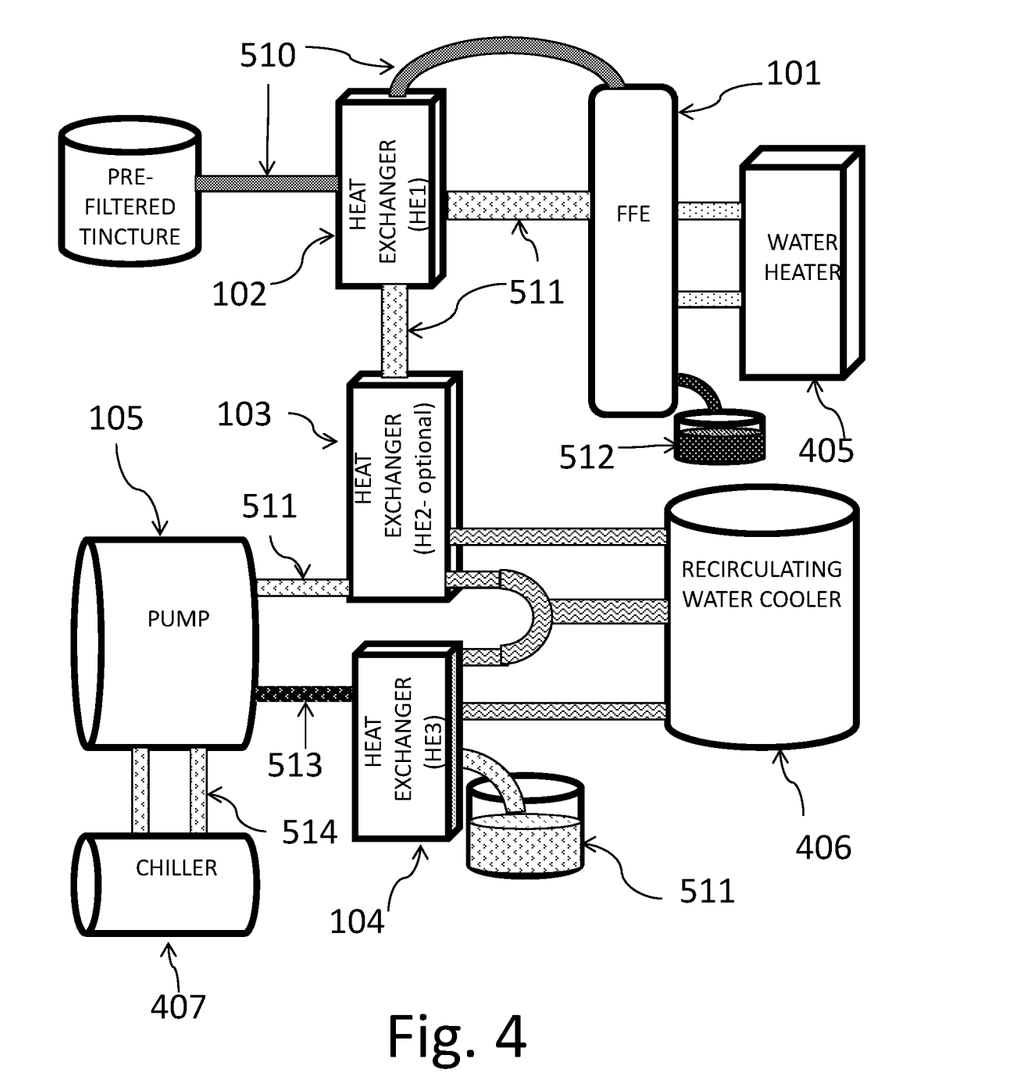
FIG. 4 is a schematic view of an embodiment of components and their connections.

FIGS. 2, 3 and 4 depict some versions of the process and equipment. Embodiments of the cannabinoid mixture 510 (FIG. 4), such as a solution or tincture, which can be pre-filtered, can be connected to the first heat exchanger (HE1) 102. Examples of the pump 105 can pull a vacuum on portions or all of the system, which can be a closed loop system, or even consist of a closed loop system. The pump 105 can move the cannabinoid mixture 510 into HE1 102. HE1 102 can be heated using solvent vapor 511 from the falling film evaporator 101. HE1 102 can pre-heat the cannabinoid mixture 510 to below its boiling point (e.g., approximately 70 degrees C.) in one example. The pre-heated cannabinoid mixture 510 can be drawn into the top of the falling film evaporator 101.

Figure 5:
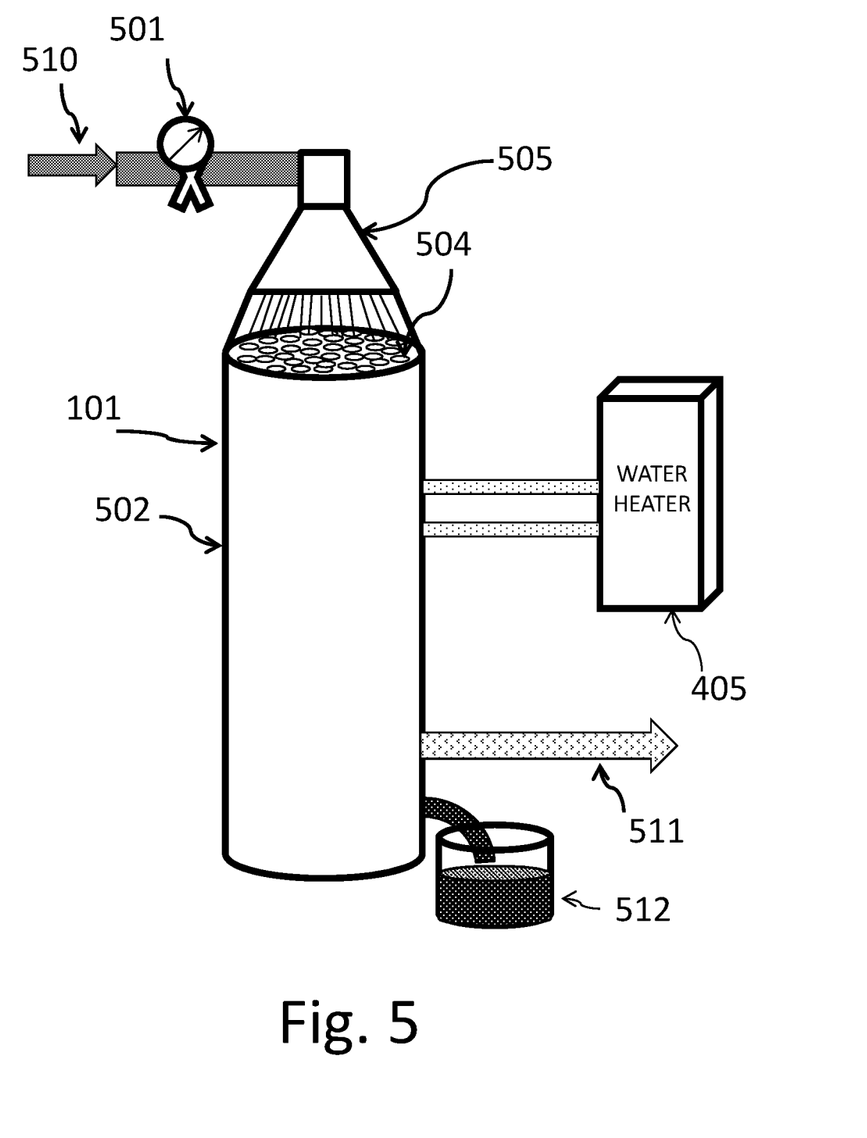
FIG. 5 is a schematic view of an embodiment of a falling film evaporator system.

As shown in FIG. 5, embodiments of the falling film evaporator 101 can include a metering valve 501, a container (e.g., cylinder) 502, evaporation tubes 504 and a distribution mechanism 505. The evaporation tubes 504 can extend along the length of the cylinder 502. An external heater 405 can provide heated water or other liquid that can be circulated around the evaporation tubes 504, such as around their exteriors. The system can be sealed such that the vacuum drawn by the pump 105 pulls the cannabinoid mixture 510 into the system. The cannabinoid mixture 510 can go through the metering valve 501 and then into the distribution mechanism 505, which can evenly distribute the cannabinoid mixture 510 among the heated evaporation tubes 504. This can form a laminar flow along interior walls of the evaporation tubes 504. As the cannabinoid mixture 510 falls through the evaporation tubes 504, thin films of the cannabinoid mixture 510 are formed. The solvent can exceed its boiling point and can boil off into a complete solvent vapor. The remaining cannabinoid material can then flow down and out of the falling film evaporator 101 in the form of cannabinoid crude oil 512.

In some embodiments, the solvent 511 that now can be in a substantially vapor form or complete vapor stream, can be drawn from the falling film evaporator 101 by the vacuum from pump 105 and into HE1 102. This solvent 511 can be used to pre-heat subsequent cannabinoid mixture 510 that is being fed into the system. The solvent 511 can be drawn further through the process toward the pump 105. At this point, the solvent 511 may be passed through a second heat exchanger (HE2) 103 to cool it in preparation for entry into the pump 105. The HE2 103 is optional. It can be included depending on, for example, the efficiency of the overall system and the boiling point of the solvent 511 that is selected.

Examples of the pump 105 can include a commercially available liquid ring distillation pump. Such a pump can have high vacuum performance for liquid and vapor. For example, the pump 105 can be capable of forming a vacuum of about 22 to about 29 inches of mercury or Hg (200 to 20 Torr). Other suitable pumps can be used. If a liquid ring distillation pump is used, the liquid 514 used for the ring in the pump 105 can be the same material as the solvent 511. Such a selection can help ensure that the solvent 511 is not contaminated with any other foreign material. However, a different liquid or a different concentration of the solvent can be used. The liquid 514 supplied for a liquid ring pump can be cooled by a chiller 407. Examples of the chiller 407 can be a glycol cooled chiller for enhanced efficiency. In the event that a different type of pump is used, an appropriate cooling system may be used to appropriately cool and condense the mixture.

Figure 6:
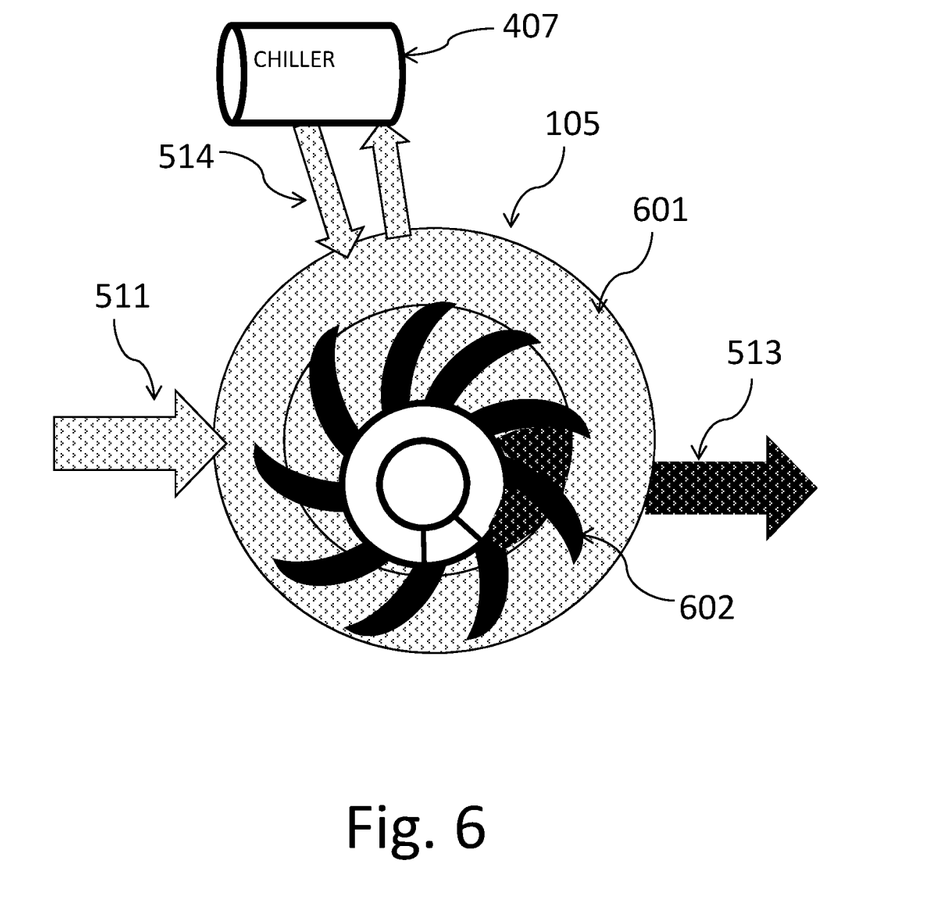
FIG. 6 is a schematic view of an embodiment of a liquid ring pump system.

FIG. 6 illustrates an embodiment of the liquid flow when a liquid ring pump is used. For example, the impeller 602 of the pump 105 can be positioned eccentric to the centerline of the pump body. The pump 105 can perform a centrifugal action to circulate the internal liquid 514 as a liquid ring 601 and pull a vacuum on the inlet line. In some versions, this action can drive the entire movement of the cannabinoid mixture 510 through the system after processing through the falling film evaporator 101. See, e.g., FIG. 3. Portion of the contents or the entire contents of the system can be moved by the action of the pump, drawn or pulled by the vacuum, and/or evacuated into subsequent components of the system. Alternatively, one or more other pumps may be used as well.

Embodiments of the output 513 from the pump 105 can be the solvent 511 in liquid form at about 10 to about 20 degrees C., and at atmospheric pressure. However, the output 513 also may have some remaining vapor. The output 513 can then be processed through a third heat exchanger (HE3) 104. HE3 104 can help keep vapor from escaping from the system. In one version, HE3 104 can comprise or consist of a closed loop system that condenses any remaining vapors to recover as much of the original liquid solvent 511 as possible. Although a liquid ring pump has been shown and described, any suitable pump type may be used to draw the liquid and vapor through the system. In an example, the pump 105 can condense the solvent to form a mostly liquid mixture.

Many modifications and variations of this invention may be made without departing from its spirit and scope, as will be appreciated by those skilled in the art. For example, the specific temperatures in the foregoing discussion have been optimized for use of ethanol as the solvent, however, any other solvent may be used, and the various steps may be adjusted to optimize for that solvent. The specific embodiments described herein are offered by way of example only. The embodiments were chosen and described in order to best explain the principles of the invention and its practiced applications.

This disclosure can provide a more energy efficient process that not only separates the cannabinoids from the solvent, but also allows recovery of the solvent itself so that it can be reused. When using ethanol as the solvent, embodiments can recover 95% or more of the ethanol by volume. In addition, greater energy efficiency can be gained by re-purposing heat used by the system with one or more heat exchangers. For further efficiency, the process can be operated continuously, as a steady flow, rather than as a batch process.

Embodiments of the present disclosure can include a method and apparatus that separates cannabinoids from a solvent using a falling film evaporator in conjunction with a liquid ring or other commercially available pump. The process can begin after a solvent, such as ethanol, is used to form a cannabinoid tincture. In an example, a self-priming pump can be used to draw a vacuum on the system, and move the pre-heated mixture into a heat exchanger and then into a falling film evaporator. The heat exchanger can pre-heat the subsequent mixture to, in one version, approximately 70 degrees C. Embodiments of the pre-heat step can include a temperature in a range of about 40 to about 90 degrees C., or a range of about 50 to about 55 degrees C. Embodiments of the pressure of the pre-heat step can be in a range of about 22 to about 29 inches Hg (200 to 20 Torr), or in a range of about 25 to about 28 inches Hg (125 to 50 Torr), or about 26 inches Hg (100 Torr).

In the falling film evaporator, the mixture can be heated above the boiling point of the solvent. In the case of ethanol, this can be approximately 90 degrees C., in one embodiment. With the solvent boiled off, the purified cannabinoid crude oil can be separated out and siphoned off the bottom of the falling film evaporator. Examples of the solvent vapor can be moved by the vacuum of the pump back into the initial heat exchanger to provide pre-heating for subsequent mixture that is being fed into the system.

In some embodiments, the mixture from the heating side of an initial heat exchanger can be a mixture of solvent vapor and condensate. For ethanol, one version of the temperature can be close to its boiling point at a selected pressure. For example, the temperature can be approximately 78 degrees C., which is the boiling point at atmospheric pressure. The liquid and vapor solvent can be drawn by the pump vacuum through another heat exchanger. The liquid and vapor solvent can be cooled via water or another coolant of the second heat exchanger, to cool and further condense the solvent to its liquid form. For ethanol, the mixture from the heat exchanger can be approximately 50 degrees C., in one version. The cooled solvent from this second heat exchanger can be circulated directly into the pump for collection, further condensing, etc. The liquid and vapor solvent can be primarily liquid, but it also can have remaining solvent in vapor form. It can be routed to a final heat exchanger that converts any remaining solvent vapor to liquid solvent. The liquid solvent from the final heat exchanger can be substantially pure or pure solvent condensate in liquid form at, for example, room temperature. The recovered liquid solvent can then be reused as needed.

Other embodiments can include one or more of the following items.

A system for processing cannabinoids and recovering solvent, the system comprising:

a vessel configured to contain a mixture comprising cannabinoids and solvent;

a pump configured to form a vacuum in the system to draw the mixture into a first heat exchanger configured to pre-heat the mixture to less than a boiling point of the solvent;

a falling film evaporator configured to receive the mixture from the first heat exchanger, heat the mixture above the boiling point of the solvent, and boil the mixture to form a solvent vapor, and the falling film evaporator is configured to collect the cannabinoids from the mixture as a crude oil;

the first heat exchanger is configured to receive the solvent vapor, the system is configured to transfer heat to incoming mixture of the system, thereby configured to cool and condense the solvent vapor to not greater than the boiling point of the solvent to form solvent condensate and vapor;

a second heat exchanger configured to receive and further cool the solvent condensate and vapor to form further condensed solvent and some solvent vapor; and the pump is configured to receive the further condensed solvent and some solvent vapor and increase pressure to increase the boiling point of the solvent to form solvent liquid, such that the system is configured to recover solvent liquid for reuse.

The system of any of these items, further comprising a third heat exchanger configured to receive and cool the solvent liquid, such that the system is configured to recover the cooled solvent liquid for reuse.

The system of any of these embodiments, wherein the third heat exchanger is configured to operate at a temperature in a range of about 10 to about 20 degrees C.

The system of any of these items, wherein the pump is configured to operate at a temperature in a range of about 40 to about 90 degrees C.

The system of any of these items, wherein the pump is configured to operate at a pressure in a range of about 22 to about 29 inches of Hg.

The system of any of these items, further comprising a pump manifold configured to be coupled between the pump and the second heat exchanger, and a holding vessel configured to retain the cannabinoid crude oil, wherein the holding vessel is configured to be coupled between the falling film evaporator and the pump.

The system of any of these items, wherein the pump is configured to provide circulation of every fluid throughout the system.

The system of any of these items, wherein the pump consists of a liquid ring pump, and the liquid ring pump is the only pump used in the system.

The system of any of these items, further comprising a feed pump and a discharge pump.

A method for processing cannabinoids and recovering solvent, the method comprising:

forming a mixture comprising cannabinoids and solvent;

using a pump to form a vacuum in a system, drawing the mixture into a first heat exchanger and pre-heating the mixture to less than a boiling point of the solvent;

drawing the mixture into a falling film evaporator, heating the mixture above the boiling point of the solvent, and boiling the mixture to form a solvent vapor;

collecting the cannabinoids from the mixture as a crude oil at a bottom of the falling film evaporator;

drawing the solvent vapor to the first heat exchanger;

transferring heat to incoming mixture of the system, thereby cooling and condensing the solvent vapor to not greater than the boiling point of the solvent to form solvent condensate and vapor;

drawing and further cooling the solvent condensate and vapor in a second heat exchanger to form further condensed solvent and some solvent vapor;

drawing the further condensed solvent and some solvent vapor to the pump and increasing pressure to increase the boiling point of the solvent to form solvent liquid; and then drawing the solvent liquid to a third heat exchanger, cooling the solvent liquid and recovering the cooled solvent liquid for reuse.

The process of any of these items, wherein an operating temperature of step (b) is about 40 to about 90 degrees C.

The process of any of these items, wherein an operating temperature of step (b) is about 50 to about 55 degrees C.

The process of any of these items, wherein an operating pressure of step (b) is about 22 to about 29 inches of Hg.

The process of any of these items, wherein an operating pressure of step (b) is about 25 to about 28 inches of Hg.

The process of any of these items, wherein step (d) comprises drawing the crude oil into a holding vessel coupled between the falling film evaporator and the pump, and further comprising a pump manifold coupled between the pump and the second heat exchanger.

The system of any of these items, further comprising a pump manifold configured to be coupled between the pump and the second heat exchanger, and a holding vessel configured to retain the cannabinoid crude oil, wherein the holding vessel is configured to be coupled between the FFE and the pump.

The process of any of these items, wherein the pump circulates every fluid throughout the system.

The process of any of these items, wherein the pump consists of a liquid ring pump, and the liquid ring pump is the only pump used in the method.

The process of any of these items, further comprising a feed pump and a discharge pump.

The process of any of these items, wherein step (i) comprises operating in a temperature in a range of about 10 to about 20 degrees C.

A continuous method for processing cannabinoids and recovering solvent, the method comprising:

(a) forming a mixture comprising cannabinoids and solvent;

(b) using a liquid ring pump to form a vacuum in a closed loop system, drawing the mixture into a first heat exchanger and pre-heating the mixture to less than a boiling point of the solvent;

(c) drawing the mixture into a falling film evaporator, heating the mixture above the boiling point of the solvent, and boiling the mixture to form a solvent vapor;

(d) collecting the cannabinoids from the mixture as a crude oil at a bottom of the falling film evaporator;

(e) drawing the solvent vapor to the first heat exchanger;

(f) transferring heat to incoming mixture of the closed loop system, thereby cooling and condensing the solvent vapor to not greater than the boiling point of the solvent to form solvent condensate and vapor;

(g) drawing and further cooling the solvent condensate and vapor in a second heat exchanger to form further condensed solvent and some solvent vapor;

(h) drawing the further condensed solvent and some solvent vapor to the liquid ring pump and increasing pressure to increase the boiling point of the solvent to form solvent liquid; and then (i) drawing the solvent liquid to a third heat exchanger, cooling the solvent liquid and recovering the cooled solvent liquid for reuse.

This written description uses examples to disclose the embodiments, including the best mode, and also to enable those of ordinary skill in the art to make and use the invention. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

Note that not all of the activities described above in the general description or the examples are required, that a portion of a specific activity may not be required, and that one or more further activities can be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

It can be advantageous to set forth definitions of certain words and phrases used throughout this patent document. The term "communicate," as well as derivatives thereof, encompasses both direct and indirect communication. The term "discreet," as well as derivatives thereof, references to the amount of skin exposed by a user of the garment, rather than the type of style of the garment. The terms "include" and "comprise," as well as derivatives thereof, mean inclusion without limitation. The term "or" is inclusive, meaning and/or. The phrase "associated with," as well as derivatives thereof, can mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items can be used, and only one item in the list can be needed. For example, "at least one of: A, B, and C" includes any of the following combinations: A, B, C, A and B, A and C, B and C, and A and B and C.

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function.

Benefits, other advantages, and solutions to problems have been described above with regard to specific embodiments. However, the benefits, advantages, solutions to problems, and any feature(s) that can cause any benefit, advantage, or solution to occur or become more pronounced are not to be construed as a critical, required, sacrosanct or an essential feature of any or all the claims.

After reading the specification, skilled artisans will appreciate that certain features are, for clarity, described herein in the context of separate embodiments, can also be provided in combination in a single embodiment. Conversely, various features that are, for brevity, described in the context of a single embodiment, can also be provided separately or in any subcombination. Further, references to values stated in ranges include each and every value within that range.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A system for processing cannabinoids and recovering solvent, the system comprising:
   a vessel configured to contain a mixture comprising cannabinoids and solvent;
   a pump configured to form a vacuum in the system to draw the mixture into a first heat exchanger configured to pre-heat the mixture to less than a boiling point of the solvent;
   a falling film evaporator configured to receive the mixture from the first heat exchanger, heat the mixture above the boiling point of the solvent, and boil the mixture to form a solvent vapor, and the falling film evaporator is configured to collect the cannabinoids from the mixture as a crude oil;
   the first heat exchanger is configured to receive the solvent vapor, the system is configured to transfer heat to incoming mixture of the system, thereby configured to cool and condense the solvent vapor to not greater than the boiling point of the solvent to form solvent condensate and vapor;
   a second heat exchanger configured to receive and further cool the solvent condensate and vapor to form further condensed solvent and some solvent vapor; and the pump is configured to receive the further condensed solvent and some solvent vapor and increase pressure to increase the boiling point of the solvent to form solvent liquid, such that the system is configured to recover solvent liquid for reuse.

2. The system of claim 1, further comprising a third heat exchanger configured to receive and cool the solvent liquid, such that the system is configured to recover the cooled solvent liquid for reuse.

3. The system of claim 2, wherein the third heat exchanger is configured to operate at a temperature in a range of about 10 to about 20 degrees C.

4. The system of claim 1, wherein the pump is configured to operate at a temperature in a range of about 40 to about 90 degrees C.

5. The system of claim 1, wherein the pump is configured to operate at a pressure in a range of about 22 to about 29 inches of Hg.

6. The system of claim 1, further comprising a pump manifold configured to be coupled between the pump and the second heat exchanger, and a holding vessel configured to retain the cannabinoid crude oil, wherein the holding vessel is configured to be coupled between the falling film evaporator and the pump.

7. The system of claim 1, wherein the pump is configured to provide circulation throughout the system.

8. The system of claim 1, wherein the pump consists of a liquid ring pump, and the liquid ring pump is the only pump used in the system.

9. A method for processing cannabinoids and recovering solvent with the system of claim 1, the method comprising:
   (a) forming the mixture comprising cannabinoids and solvent;
   (b) using the pump to form the vacuum in the system, drawing the mixture into the first heat exchanger and pre-heating the mixture to less than a boiling point of the solvent;
   (c) drawing the mixture into the falling film evaporator, heating the mixture above the boiling point of the solvent, and boiling the mixture to form a solvent vapor;
   (d) collecting the cannabinoids from the mixture as a crude oil at a bottom of the falling film evaporator;
   (e) drawing the solvent vapor to the first heat exchanger;
   (f) transferring heat to incoming mixture of the system, thereby cooling and condensing the solvent vapor to not greater than the boiling point of the solvent to form solvent condensate and vapor;
   (g) drawing and further cooling the solvent condensate and vapor in the second heat exchanger to form further condensed solvent and some solvent vapor;
   (h) drawing the further condensed solvent and some solvent vapor to the pump and increasing pressure to increase the boiling point of the solvent to form solvent liquid; and then
   (i) drawing the solvent liquid to the third heat exchanger, cooling the solvent liquid and recovering the cooled solvent liquid for reuse.

10. The process of claim 9, wherein an operating temperature of step (b) is about 40 to about 90 degrees C.

11. The process of claim 9, wherein an operating temperature of step (b) is about 50 to about 55 degrees C.

12. The process of claim 9, wherein an operating pressure of step (b) is about 22 to about 29 inches of Hg.

13. The process of claim 9, wherein an operating pressure of step (b) is about 25 to about 28 inches of Hg.

14. The process of claim 9, wherein step (d) comprises drawing the crude oil into a holding vessel coupled between the falling film evaporator and the pump, and further comprising a pump manifold coupled between the pump and the second heat exchanger.

15. The system of claim 9, further comprising a pump manifold configured to be coupled between the pump and the second heat exchanger, and a holding vessel configured to retain the cannabinoid crude oil, wherein the holding vessel is configured to be coupled between the FFE and the pump.

16. The process of claim 9, wherein the pump circulates every fluid throughout the system.

17. The process of claim 9, wherein the pump consists of a liquid ring pump, and the liquid ring pump is the only pump used in the method.

18. The process of claim 9, wherein step (i) comprises operating in a temperature in a range of about 10 to about 20 degrees C.

19. A continuous method for processing cannabinoids and recovering solvent using the system of claim 1, the method comprising:
- (a) forming the mixture comprising cannabinoids and solvent;
- (b) using a liquid ring pump to form a vacuum in a closed loop system, drawing the mixture into a first heat exchanger and pre-heating the mixture to less than a boiling point of the solvent;
- (c) drawing the mixture into the falling film evaporator, heating the mixture above the boiling point of the solvent, and boiling the mixture to form a solvent vapor;
- (d) collecting the cannabinoids from the mixture as a crude oil at a bottom of the falling film evaporator;
- (e) drawing the solvent vapor to the first heat exchanger;
- (f) transferring heat to incoming mixture of the closed loop system, thereby cooling and condensing the solvent vapor to not greater than the boiling point of the solvent to form solvent condensate and vapor;
- (g) drawing and further cooling the solvent condensate and vapor in the second heat exchanger to form further condensed solvent and some solvent vapor;
- (h) drawing the further condensed solvent and some solvent vapor to the liquid ring pump and increasing pressure to increase the boiling point of the solvent to form solvent liquid; and then
- (i) drawing the solvent liquid to the third heat exchanger, cooling the solvent liquid and recovering the cooled solvent liquid for reuse.

* * * * *